US007893216B2

(12) United States Patent
Liu et al.

(10) Patent No.: US 7,893,216 B2
(45) Date of Patent: Feb. 22, 2011

(54) ANTI-HUMAN TRAIL RECEPTOR DR5 MONOCLONAL ANTIBODY (AD5-10), METHOD THEREOF AND USE OF THE SAME

(75) Inventors: Yanxin Liu, Beijing (CN); Yabin Guo, Beijing (CN); Dexian Zheng, Beijing (CN)

(73) Assignee: The Institute of Basic Medical Sciences of Chinese Academy of Medical Sciences, Beijing (CN)

( * ) Notice: Subject to any disclaimer, the term of this patent is extended or adjusted under 35 U.S.C. 154(b) by 1097 days.

(21) Appl. No.: 11/596,271

(22) PCT Filed: Mar. 7, 2005

(86) PCT No.: PCT/CN2005/000271

§ 371 (c)(1),
(2), (4) Date: Nov. 10, 2006

(87) PCT Pub. No.: WO2006/017961

PCT Pub. Date: Feb. 23, 2006

(65) Prior Publication Data

US 2010/0080806 A1    Apr. 1, 2010

(30) Foreign Application Priority Data

Aug. 19, 2004    (CN) .................. 2004 1 0070093

(51) Int. Cl.
C12P 21/08 (2006.01)
C07K 16/00 (2006.01)
A61K 39/395 (2006.01)
C12N 5/07 (2010.01)
C12N 5/16 (2010.01)

(52) U.S. Cl. .............. 530/388.1; 424/130.1; 424/138.1; 424/141.1; 424/155.1; 435/326; 435/330; 530/387.1; 530/388.22; 530/388.8

(58) Field of Classification Search .................. None
See application file for complete search history.

(56) References Cited

U.S. PATENT DOCUMENTS

2003/0133932 A1* 7/2003 Zhou et al. ............... 424/143.1

FOREIGN PATENT DOCUMENTS

CN    1388135    1/2003

OTHER PUBLICATIONS

Rudikoff, Giusti, Cook and Scharff. Single amino acid substitution altering antigen-binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an anti-ErbB2 antibody obtained by shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Ezzell, C. Cancer "vaccines": an idea whose time has come? The Journal of NIH Research, 1995. vol. 7, pp. 46-49.*
Forni, G., Lollini, P.L., Musiani, P., and Colombo, M.P. Immunoprevention of Cancer. Cancer Research, 2000. vol. 60, pp. 2571-2575.*
Donnelly, J. Cancer vaccine targets leukemia. Nature Medicine, 2003. vol. 9 No. 11, pp. 1354-1356.*
Degruijl, T.D., and Curiel, D.T. Cancer vaccine strategies get bigger and bigger. Nature Medicine, 1999. vol. 5 No. 10, pp. 1124-1125.*
Chattergee, M.B., Foon, K.A., and Kohler, H. Idiotypic antibody immunotherapy of cancer. Cancer Immunology and Immunotherapy, 1994. vol. 38, pp. 75-82.*
Bodey, B., Bodey Jr., B., Siegel, S.E., and Kaiser, H.E. Failure of cancer vaccines: the significant limitations of this approach to immunotherapy. Anticancer Research, 2000. vol. 20, pp. 2665-2676.*
Lee, Wang, Nielson, Wunderlich, Migueles, Connors, Steinberg, Rosenberg, and Marincola, Increased vaccine-specific T cell frequency after peptide-based vaccination correlates with increased susceptibility to in vitro stimulation but does not lead to tumor regression. Journal of Immunology, 1999. vol. 163, pp. 6292-6300.*

* cited by examiner

*Primary Examiner*—Anne M. Gussow
(74) *Attorney, Agent, or Firm*—Fulbright & Jaworski LLP (57) ABSTRACT

The present invention discloses a monoclonal antibody against the extracellular domain of human tumor necrosis factor-related apoptosis-inducing ligand receptor DR5 (death receptor 5). The present invention also provides a method of producing the monoclonal antibody, amino acid sequences of the variable regions of the monoclonal antibody's heavy chain and light chain, as well as use of the monoclonal antibody for preparation of a medicament in the treatment of various cancers and/or AIDS.

5 Claims, 5 Drawing Sheets

ANTI-HUMAN TRAIL RECEPTOR DR5 MONOCLONAL ANTIBODY (AD5-10), METHOD THEREOF AND USE OF THE SAME

FIELD OF THE INVENTION

This invention involves a monoclonal antibody (mAb) (named as AD5-10) against human tumor necrosis factor-related apoptosis-inducing ligand (TRAIL) receptor DR5; the hybridoma strain producing the mAb, amino acid sequences of the heavy chain and light chain variable region and method thereof as well as use of the same, especially, in method of generating murine anti-human DR5 mAb by immunizing mice with recombinant DR5 extracellular region and the property and the use of the mAb. The murine anti-human DR5 mAb of this invention and its Fab and F(ab')$_2$ can be used alone or in combination with TRAIL or other chemotherapeutic agents to have significant therapeutic effects on cancers and AIDS. Also, the gene of the mAb can be linked to proper vectors for the gene therapy of cancers and AIDS.

BACKGROUND OF THE INVENTION

The death receptors, belonging to the tumor necrosis factor receptor (TNFR) super family, are characterized by their cysteine rich domains in the extracellular region and death domains (DD) in the intracellular region. Death domain endows death receptor with function of inducing cell death by apoptosis, but sometime it also mediates other signals. Tumor necrosis factor-related apoptosis-inducing ligand, TRAIL (Wiley S R, Schooley K, Smolak P, et al., Identification and characterization of a new member of the TNF family that induces apoptosis, Immunity, 1995, 3:673-682) in combination with its death domains triggers two cell death signaling pathways, i.e., death receptor pathway and mitochondrion pathway, to kill various tumor cells, but is nontoxic to most normal human cells. Human T lymphocytes infected by HIV are more susceptible to TRAIL/TRAIL receptor-induced cytotoxicity than the normal T cells. These studies suggested attractive prospects of TRAIL and TRAIL receptor in the therapy of cancer and AIDS.

Five TRAIL receptors, i.e., DR4 (death receptor 4 or named as TRAIL-R1), DR5 (death receptor 5, or named as TRAIL-R2/TRICK2/KILLER), DcR1 (decoy receptor 1 or named as TRID/TRAIL-R3/LIT), DcR2 (TRAIL-R4 or named as TRUNDD), and osteoprotegerin (OPG), have been identified up to date. DR4 and DR5 possess functional intracellular death domain and can mediate apoptosis signals. DcR1 is anchored on the cell membrane via glycosyl phosphatidyl inositol (GPI) and contains no death domain at all, so that it cannot mediate cell death signals. DcR2 has an incomplete death domain, which neither mediate cell death signals. DcR1 can inhibit TRAIL to bind with a death domain as a receptor. DcR2 having an incomplete death domain serves as decoy receptors to inhibit the killing activity of TRAIL by competing association with TRAIL. Osteoprotegerin is a secretive receptor for TRAIL and can bind with TRAIL and inhibits TRAIL functions.

It was showed in prior art that mAbs against DR4 or DR5 could kill tumor cells without toxicity to normal cells. However, since the extracellular domain of DR4 or DR5 comprises various epitopes, the relationship between the biological activity of mAbs and the relevant epitopes have not been defined by known technologies.

SUMMARY OF THE INVENTION

The first objective of this invention is to provide a monoclonal antibody against human TRAIL receptor DR5 (named as AD5-10), having amino acid sequences of heavy and light chain variable regions as described in the Sequence List.

The second objective of this invention is to provide a method for generating the anti-human TRAIL receptor (DR5) monoclonal antibody (AD5-10).

The third objective of this invention is to provide a hybridoma strain producing anti-human TRAIL receptor (DR5) monoclonal antibody (AD5-10).

The fourth objective of this invention is to provide a monoclonal antibody, whose subtype is IgG3κ.

The fifth objective of this invention is to provide a monoclonal antibody that induces apoptosis in various tumor cell lines in vitro.

The sixth objective of this invention is to provide a monoclonal antibody that inhibits the formation and growth of human tumor in nude mice.

The seventh objective of this invention is to provide a monoclonal antibody that induces different cell signals from those induced by TRAIL in certain cell lines.

The eighth objective of this invention is to provide a monoclonal antibody that significantly synergizes with TRAIL to enhance the tumoricidal activity.

The ninth objective of this invention is to provide use of whole molecule, Fab, F(ab')$_2$, and single chain Fv (ScFv) of the said monoclonal antibody, or human-mouse chimeric antibodies and reshaped antibodies constructed by genetically engineering technology in developing therapeutic agents for treatment of cancer and/or AIDS.

The tenth objective of this invention is to provide a monoclonal antibody whose gene can be linked to certain vectors in preparation of anti-cancer and/or anti-AIDS agents.

The eleventh objective of this invention is to provide combined use of the said monoclonal antibody with chemotherapeutic agents, e.g. 8-chloro-adenosine, 5-Fu, and actinomycin D, to enhance tumoricidal activity, reduce the dose of chemotherapeutic agents, significantly boost curative effect and reduce toxic and side effects.

In order to achieve the objective as mentioned above, the present invention is to provide a murine monoclonal antibody comprising amino acid sequence of a light chain variable region (VL) having SEQ ID No. 1, and amino acid sequence of a heavy chain variable region (VH) having SEQ ID No. 2.

The said amino acid sequences of light chain variable region respectively consist of the sequences of:

```
CDR1:  Arg Ser Ser Gln Ser Leu Val His Ser Asn Gly Asn Thr Tyr Leu His;
       24                  30                  35                  39

CDR2:  Lys Val Ser Asn Arg Phe Ser;
       55                      61
and

CDR3:  Phe Gln Ser Thr His Val Pro His Thr.
       94                  100     102
```

These correspond to amino acids 24-39, 55-61, and 94-102 of SEQ ID NO: 1, respectively.

The said amino acid sequences of heavy chain variable region respectively consist of the sequences of:

```
CDR11: Asp Phe Ser Met Asn;
       31              35

CDR22: Trp Ile Asn Thr Glu Thr Gly Glu Pro Thr Tyr Ala Asp Asp Phe Lys Gly;
       50              55              60                      65  66

CDR33: Ile Asp Tyr.
       99      101
```

These correspond to amino acids 31-35, 50-66 and 99-101 of SEQ ID NO: 2, respectively.

The present invention is also to provide a method for generating TRAIL receptor DR5 extracellular domain mAb, wherein the mAb comprises amino acid sequence of a light chain variable region (VL) having SEQ ID No. 1, and amino acid sequence of a heavy chain variable region (VH) having SEQ IP No. 2. The method comprises the steps of:

amplifying the DR5 extracellular domain cDNA by using human DR5 cDNA as template and polymerase chain reaction (PCR), and cloning amplified cDNA into prokaryotic expressing vector to have an expression plasmid;

transforming the expression plasmid into *E. coli* to obtain the genetically engineered bacteria strain that express DR5 extracellular domain, culturing the bacteria strain to have recombinant DR5 extracellular protein;

immunizing mice with recombinant DR5 extracellular protein, syncretizing murine spleen cells with SP2/O myeloma cells to prepare a hybridoma named as AD5-10 that produces a monoclonal antibody.

The hybridoma strain produced by the above steps of method has been deposited in China General Microbiological Culture Collection Center on Jul. 16, 2004 with the classified name of BALB/c mouse hybridoma, and deposition Number of CGMCC 1192.

The hybridoma strain of the present invention is able to produce monoclonal antibody, and the subtype of immunoglobulin of the monoclonal antibody produced is IgG3κ.

In addition, monoclonal antibody produced by the said hybridoma strain is named as AD5-10. Such antibody as well as TRAIL can bind with DR5 at the site different from that of TRAIL.

The said hybridoma strain is able to produce a monoclonal antibody AD5-10 that has strong tumoricidal activity in vitro. The said monoclonal antibody AD5-10 does synergize with TRAIL and other chemotherapeutic agents in killing tumor cells as well as in inhibiting growth and formation of immigrated human tumors in nude mice.

The said monoclonal antibody AD5-10 produced by the said hybridoma strain induces both caspase-dependent and -independent apoptotic signal pathways, and triggers different signaling pathway from those triggered by TRAIL in suitable cell lines.

The present invention is further to provide a use of IgG of murine monoclonal antibody AD5-10 in the preparation of medicament for treatment of cancers and/or AIDS; and to provide a use of the murine monoclonal antibody AD5-10 and its Fab or F(ab')$_2$ or combination of Fc with 80% identity sequence of the murine monoclonal antibody in preparation of a recombinent single antibody agent for the treatment of cancers and/or AIDS.

Additionally, the present invention is further to provide a use of the murine monoclonal antibody and its Fab or F(ab')$_2$ or combination of Fc of human IgG with 80% identity sequence of the murine monoclonal antibody to form a mouse-human chimeric antibody in preparation of a medicament for the treatment of cancers and/or AIDS.

The present invention is also to provide a use of the complete murine monoclonal antibody or 80% identity sequence of the murine monoclonal antibody in preparation of a reshaped monoclonal antibody.

Finally, according to the present invention, a use of Fab or F(ab')$_2$ or 80% identity sequence of the Fab or F(ab')$_2$ of the said murine monoclonal antibody in combination with pharmaceutical acceptable vectors in preparation of a gene therapeutic agent for the treatment of cancers and/or AIDS.

So as mentioned above, the present invention has applied modern biological technology and method such as genetically-engineering process and provides with a method of a soluble recombinant protein of TRAIL receptor DR5 extracellular domain, so that the recombinant protein is used as antigen to immunize BALB/c mice by hybridoma technology in order to obtain an anti-TRAIL receptor DR5 mAb, AD5-10. The amino acid sequences of heavy and light chain variable regions of this mAb are obtained by cDNA cloning to confirm that this antibody is a novel and unreported anti-DR5 mAb which subtype is IgG3κ. This mAb strongly induces apoptosis activity in various tumor cell lines in vitro and significantly inhibits the formation and growth of human tumors in nude mice. It is demonstrated in the first time that this mAb synergizes with TRAIL for promotion of killing tumor cells. This mAb can also be used with other chemotherapeutic agents to kill tumor cells both in vitro and in vivo, enhancing the curative effect and reducing the dose and toxicity of chemotherapeutic agents. Therefore, this monoclonal antibody is significant in development of novel drugs for anti-cancer and/or anti-AIDS.

In other words, the present invention relates to a monoclonal antibody AD5-10 against human TRAIL receptor DR5, whose heavy chain and light chain variable regions have amino acid sequences as described in the Sequence List.

It is also provided a method of preparing an anti-human TRAIL receptor DR5 mAb, AD5-10, mainly comprising that:

A cDNA encoding for the human TRAIL receptor DR5 extracellular domain is amplified by polymerase chain reaction (PCR) and the full length cDNA of human DR5 as template;

The cDNA is then inserted into a prokaryotic expressing vector to construct an expression plasmid that expresses DR5 extracellular domain;

The engineered bacteria strain that expresses DR5 extracellular domain is established in *E. coli* transformed with recombined expression plasmid;

The recombinant peptide of DR5 extracellular region is obtained from the bacteria after the said engineering bacteria strain that expresses DR5 extracellular domain is cultured, induced, separated and purified;

The hybridoma generating monoclonal antibody (named as AD5-10) against human TRAIL receptor DR5 is obtained after screen by immunizing mouse with the recombinant protein of DR5 extracellular region and then the mouse spleen cells are fused with SP2/0 myeloma cells.

The hybridoma obtained by the present method of the invention was deposited in China General Microbiological Culture Collection Center on Jul. 16, 2004 with the classified name of BALB/c mouse hybridoma, and deposition Number of CGMCC 1192.

This invention also relates to a use of the monoclonal antibody in preparation of drugs for the therapy of cancers and/or AIDS. The said antibody and its gene-engineering derivatives could be used in development of drugs for the therapy of variety of cancers and/or AIDS.

In other words, this invention is to amplify a cDNA encoding the extracellular domain of the human TRAIL receptor DR5, and clone the cDNA into prokaryotic vector to construct the expression plasmid to express DR5 extracellular domain with the full-length cDNA of human DR5 as template. The expression plasmid is transformed into *E. coli* to establish the engineering bacteria expressing DR5 extracellular region. The recombinant protein of DR5 extracellular region is obtained from the bacteria after the said engineering bacteria strain that expresses DR5 extracellular domain is cultured, induced, separated and purified. Mice are immunized with the recombinant protein and the spleen cells from the mice are fused with SP2/0 myeloma cells to establish the hybridoma cells generating anti-human TRAIL receptor DR5 monoclonal antibody. The hybridoma is named as AD5-10. The prokaryotic vector used in this invention is pET15-b and the strain of the *E. coli* is BL21 (DE3).

The IgG subtype of the monoclonal antibody DR5 in the present invention is IgG3 that can specifically bind with DR5, and can also bind with DR5 with TRAIL at the same time to induce and strengthen killing function of tumor cells such as liver and lung cancer. It is indicated that DR5 mAb can synergize the tumoricidal activity with TRAIL to tumor cells, and to promote DR5 to transmit apoptotic signals.

Studies in vitro have been shown that the mAb DR5 kills leukemia, liver and lung cancer cells with dose-dependent manner.

Studies in vivo have been shown that the mAb DR5 strongly suppresses the tumor formation and growth, such as human leukemia, liver and lung cancer cells in nude mice with the inhibition rate about 80% compared to the control group with longer suppression period and without rebounding on the tumor size after stop of administration.

Toxicity study shows that the mAb DR5 of the present invention does not cause observably death of the mice as well as abnormalism in appetite, function, skin and hair of the mouse and the like at the dose of 150 mg/kg during the period of 1 and 2 month's observation. Histological analysis suggests that no pathological changes in organs such as liver in mice is observable, so that this mAb is safety, functional and without toxicity and side effect.

The advantage and impact of the invention are that the unreported anti-mAb DR5 is obtained by immunizing mice with the recombinant protein of the DR5 extracellular domain and hybridoma technology. The said antibody's IgG subtype is IgG3k with novel amino acid sequences in heavy and light chain CDR region. The antibody is able to induce apoptosis of various tumor cells without toxicity to human primary normal lymphocytes in vitro and shows significant activity in suppression on the formation and growth of human liver cancer, lung carcinoma, and leukemia cells without any toxicity and side effects to the animal's organs in vivo. It also demonstrates that this mAb could be developed as novel, safe and effective anti-tumor, and anti-AIDS drugs.

In comparison with other similar home and abroad patented products, the unreported novel amino acid sequences of the heavy and light chains of the mAb with subtype of IgG3k that binds with DR5 without competition with TRAIL and synergizing tumoricidal activity with TRAIL are all unexpected by the person skilled in the art.

DETAILED DESCRIPTION OF THE DRAWINGS

FIG. 1 indicates binding of AD5-10 to human antigen DR5. Fig. A shows that AD5-10 binds with the extracellular domain of DR5 with the typical binding pattern of single site; Kd=0.3 nM (analyzed by GraphPad software); Fig. B shows that AD5-10 does not cross-react with another death receptor DR4.

FIG. 2 indicates tumoricidal activity of AD5-10 in vitro. The cell viability was determined by MTS kit (Promega). Fig. A shows that the survival rate of human T lymphocyte leukemia cells Jurkat was treated with AD5-10 at indicated concentrations for 8 hours; Fig. B shows that the survival rate of human hepatocyte carcinoma cells SMMC-7721 was treated with AD5-10 at indicated concentrations for 24 hours; Fig. C shows that the survival rate of human breast carcinoma cells MDA-MB-231 was treated with AD5-10 at indicated concentrations for 24 hours; Fig. D shows that the survival rate of human glioma cells U251 was treated with AD5-10 at indicated concentrations for 24 hours; Fig. E shows that flow cytometry of Jurkat cells was treated with AD5-10 at 100 ng/ml for 1 hour and double stained with Annexin-V and PI.

FIG. 6 indicates result of induced expression, separation and purification of protein of human DR5 extracellular domain, wherein:

in Figure A, lane 1 shows total protein of non-induced bacteria containing BL21(DE3) having empty pET15-b plasmid;

lane 2 shows total protein of bacteria induced by IPTG, containing BL21(DE3) having empty pET15-b plasmid;

lane 3 shows total protein of non-induced bacteria containing BL21(DE3) having pET15-b/DR5 plasmid;

lane 4 shows total protein of bacteria induced by IPTG, containing BL21(DE3) having empty pET15-b/DR5 plasmid, and lane 5 shows criteria of protein having lower molecular weight of 94000, 67000, 43000, 3000, 20100, 14400 kD in turn.

In Figure B, the product expressed via genetically engineered bacteria was separated and purified by Fast Protein Liquid Chromatograph (FPLC), it was indicated that all lanes means all components at 0.25-0.35M of NaCl concentration in eluent.

DETAILED DESCRIPTION OF THE INVENTION

Example 1

Two primers (P5 and P3) was synthesized according to the prior art. cDNA containing human full-length DR5 was taken as a template to carry out PCR to amplify to gene fraction of DR5 extracllular domain. The obtained gene section was linked to a prokaryotic expressing vector pET 15b (Invitrogen; USA) by cutting of Nco I and BamH I endonuclease, and transformed to E. coli BL21. The positive strain by identification was induced to express for about 4 hours under the condition of 0.1 mM Isopropy-β-D-thiogalactoside (IPTG) at 37° C. to have an expressed product, the said expressed product was purified by Fast protein liquid chromatography (FPLC) to have soluble recombinant DR5 extracellular domain protein, i.e. protein as immune agent.

```
P5:    GGCATGCCATGGAGTCTGCTCTGATCACC
       containing Nco I cutting site

P3:    GCGCGGATCCTTAGATGCCTGAGAGAGAACA
       containing BamH I cutting site
```

Figure 6:
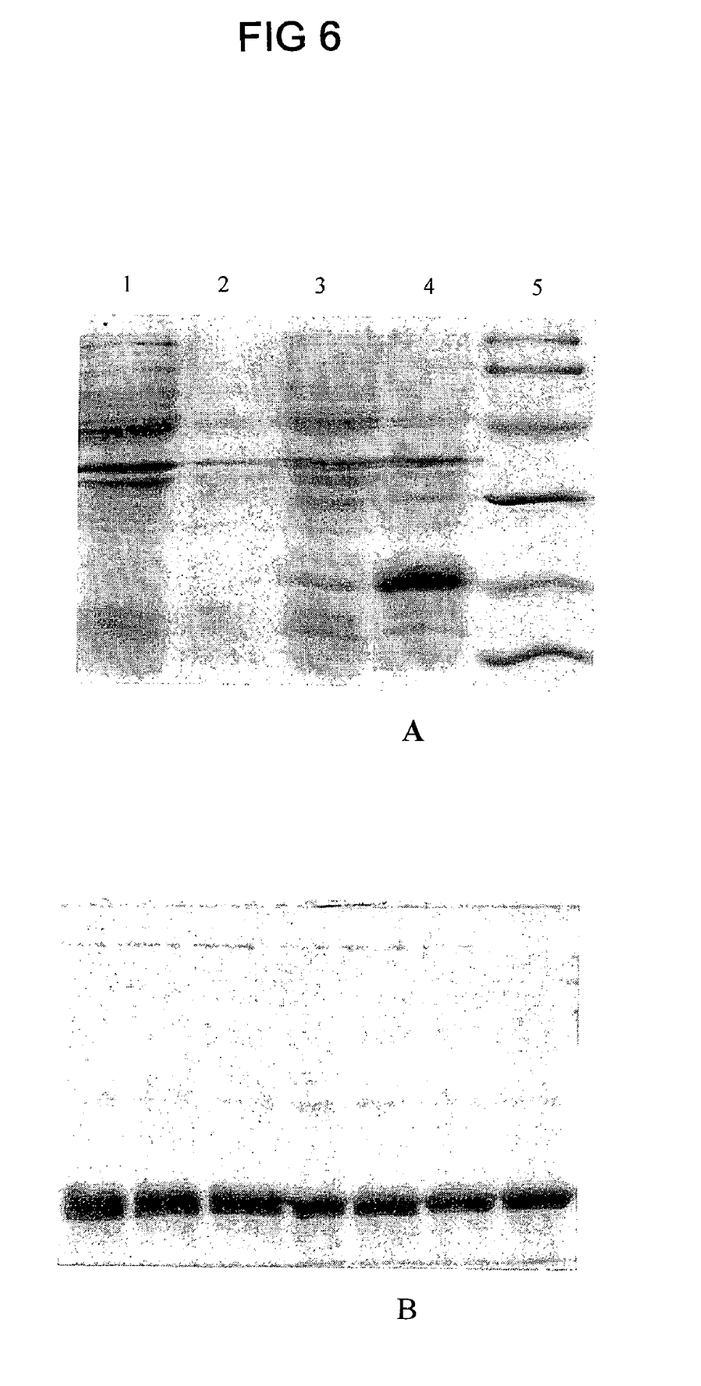

4-week-old female BALB/c mice (National Institute for the Control of pharmaceutical and biological Products, Beijing) were immunized hyodermically at abdomen 4 times with 80 g of DR5 extracellular domain protein at 2-week intervals. The mice that had antibody were immunized again with the said protein via vein injection after the blood test. Three days after the final boost, the mice died and lymphocytes from mice spleen were fused with SP2/0 myeloma cells (PEG method) and fused cells were screened and found out in HAT medium, and positive clones in were screened using ELISA method in supernatant of cell medium based on antibody titer. The result was indicated in FIG. 6.

The cultured supernatant of the positive clones made function to Jurkat cells and a cell strain capable of producing antibody for killing tumor was selected.

Example 2

ELISA was used for testing the specific combination of AD5-10 with its anitgen. ELISA plates (Costar, USA) were coated with recombinant human DR4 or DR5 extracellular domain protein expressed in E. coli over night, blocked with 5% nonfat milk at room temperature for two hours. The AD5-10 in different concentration was added at 37° C. for 4 hours and then followed by adding HRP-coupled rabbit anti-mouse IgG complex (Beijing Zhongshan Co.) for 1 hour at 37° C. o-phenylenediamines-containing chromogenic reagent (0.4 mg/ml of o-phenylenediamines, 0.045% of hydrogen peroxide, 0.73% of disodium hydrogen phosphate, 0.47% of citric acid) diluted in 1:5000 was used and the reaction was stopped by adding 2M sulfuric acid in 30 minutes. The absorbency at 492 nm was measured on a microtiter reader of enzyme-labelled machine, Wellscan MK3 (Thermo Labsystems, Finland).

Example 3

Figure 1:
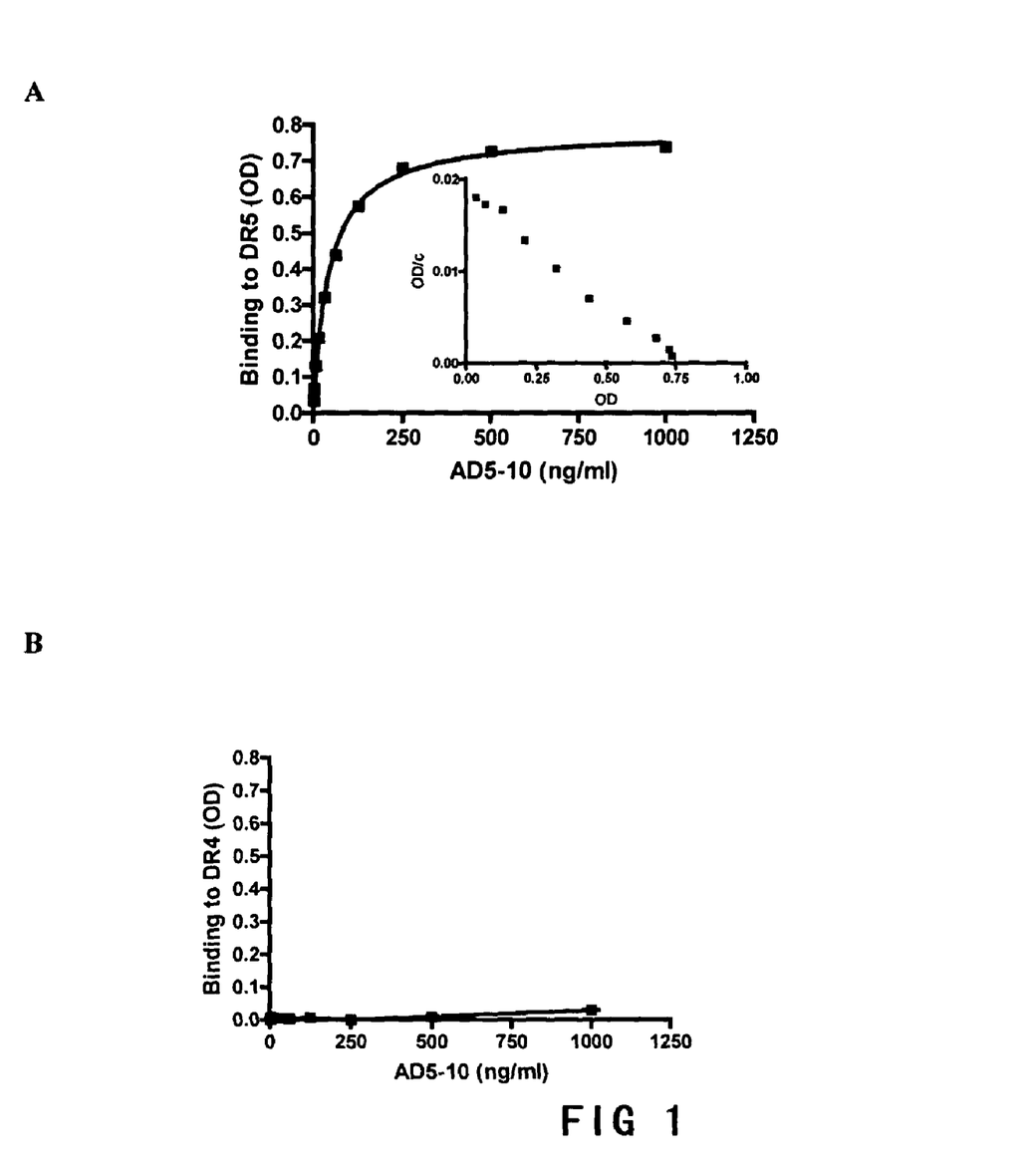
Figure 2:
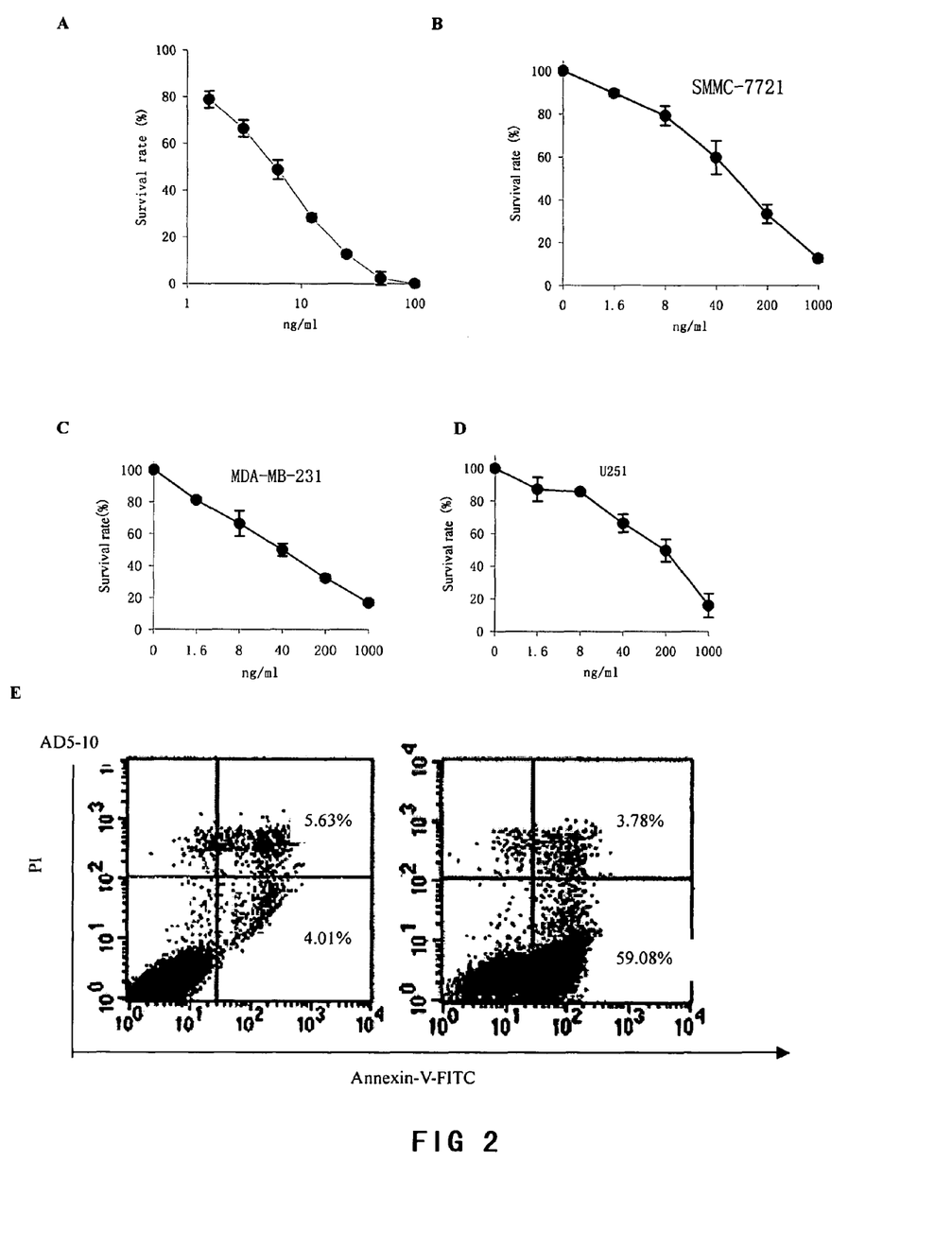
Figure 3:
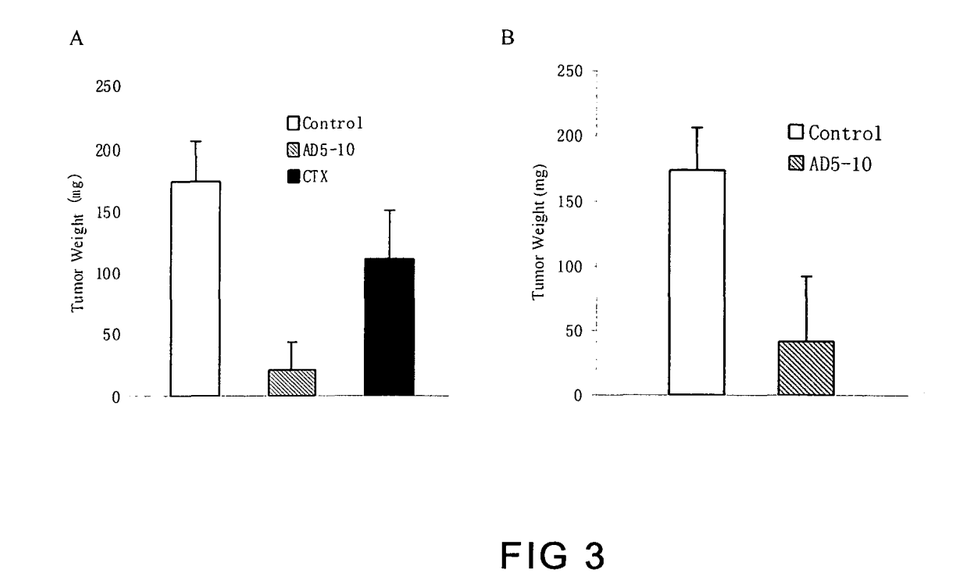
FIG. 3 indicates that AD5-10 inhibits the formation and growth of immigrated human tumor cells in nude mice, wherein Fig. A shows that AD5-10 inhibits the tumor formation of liver cancer cells SMMC-7721 in nude mice (CTX, cyclophosphamide); B, AD5-10 inhibits the tumor growth of liver cancer cells SMMC-7721 in nude mice.
Figure 4:
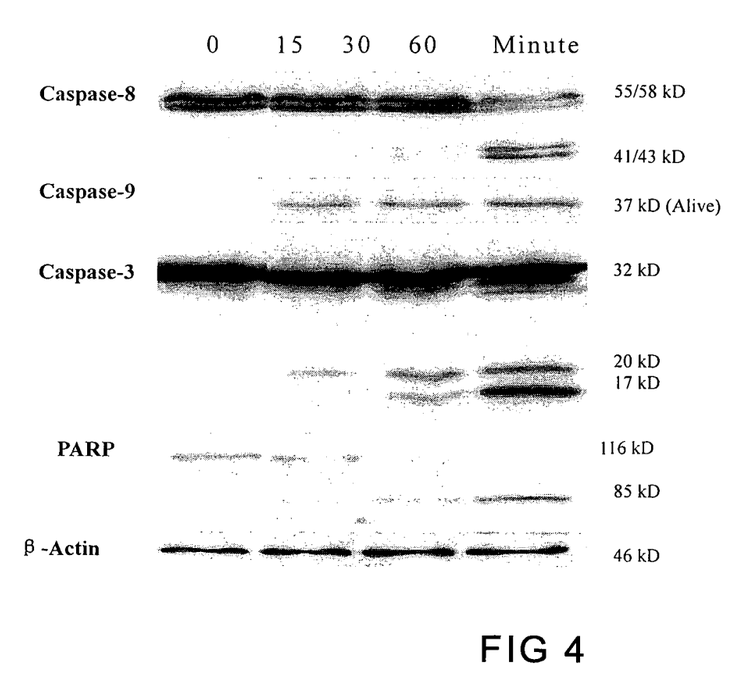
FIG. 4 indicates that AD5-10 activates caspase cascade and PARP (poly ADP-ribose polymerase) cleavage in Jurkat cells.
Figure 5:
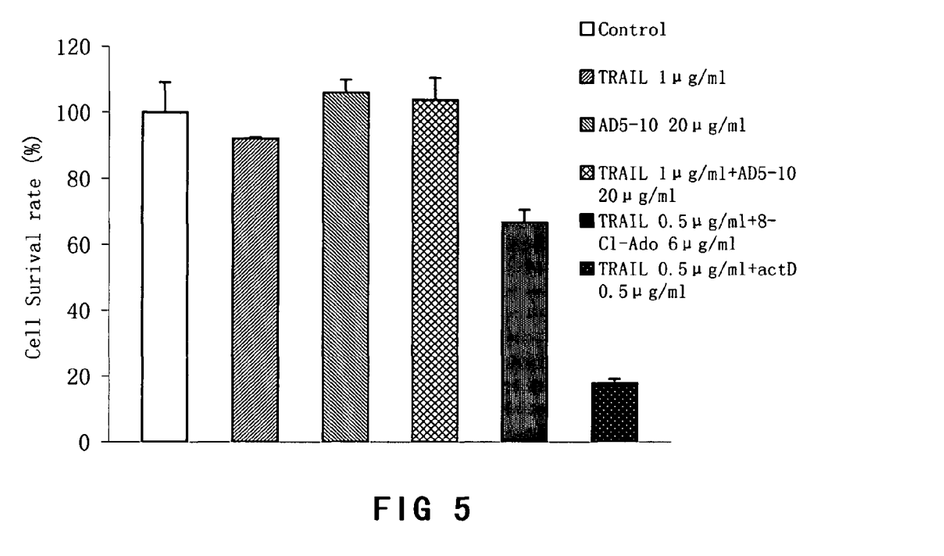
FIG. 5 indicates effect of AD5-10 to normal human primary lymphocytes was treated with AD5-10, recombinant soluble TRAIL, and chemotherapeutic agents for 24 hours in vitro. The cell viability was determined by MTS kit (Promega Co.).

MTS assay was used to determine the survival rate of tumor cells treated with AD5-10 in vitro as well as effect of AD5-10 to normal human lymphocyte in peripheral blood. Tumor cells in log growth period or newly separated normal lymphocytes in peripheral blood were cultured in 96-well plates and incubated in with different concentrations of recombinant soluble TRAIL (1 ng/ml-1000 ng/ml), AD5-10 (1 ng/ml-20000 ng/ml) and chemotherapeutic agent such as 8-chloro-adenosine (8-Cl-Ado 6 mg/ml), Dactinomycin D (act D 0.5 mg/ml). After treatment, MTS reagent (Promega, USA) was then added and reacted for 2-4 hours and the absorbance values (OD value) of each well were read by using an automatic multi-well spectrophotometer, Wellscan MK3 (Thermo Labsystems, Finland) at the wavelength of 492 nm. OD value of no cell wells is considered as "0," and the survival rate of the cells is equal to ratio of OD value of treated wells to OD value of control wells. The corresponding result is shown in FIG. 2.

Example 4

Test of AD5-10 that induces apoptosis of Hurkat cells was carried out. $10^6$ Jurkat cells in log growth period were treated with 100 ng/ml AD5-10 for 1 hour, and at the same time, untreated cells are taken as control. The treated cells were centrifuged for collection. After two times washed with phosphate-buffered saline (PBS), the collected cells were stained by means of Annexin-V/PI (Beijing Baose Co. Beijing) in ice bath for 30 minutes. The samples were analysed with a flow cytometer (EpicsXL, Beckman Coulter, USA) for testing apoptosis of the cells.

Example 5

For Analysis of AD5-10's tumoricidal Activity in vivo, nude mice BALB/c were inoculated subcutaneously with SMMC-7721 cells ($10^6$ per mouse), then the mice of early treatment group (n=10) were administrated with AD5-10 after the second days of inoculation, the inhibition activity of tumor formation was tested. The mice of late treatment group (n=10) were administrated with AD5-10 after the eighth day of inoculation, the inhibition activity of tumor formation was also tested. The dose was 15 mg/kg, three times administration in total. The mice of negative control group (n=8) were administrated with physical saline. The mice of positive control group (n=5) were administrated with cyclophosphamide (CTX, 60 mg/kg). The above administrations of AD5-10 were injected via abdomen. Three weeks later, the mice were sacrificed and the growth of tumor was determined by the weight of the tumor mass.

Example 6

Western blot analysis of caspase activation and PARP (poly ADP-ribose polymerase) cleavage induced by AD5-10 was made. Jurkat cells in log growth period were treated with 100 ng/ml AD5-10 for 0, 15, 30, and 60 minutes, then collected. After the collected cells were lysed in cell cleavage solution, SDS-PAGE was used, the proteins separated in the gel were subsequently electrotransferred onto a polyvinylidene difluoride (PVDF) membrane. The membrane was then incubated with the indicated primary antibodies (Santa Cruz, USA) and probed with HRP-conjugated secondary antibodies (Beijing Zhongshan Co.). The proteins were visualized by ECL Plus Western Blotting Detection System (Amersham Biosciences, USA).

Example 7

Cloning of the cDNA encoding for AD5-10 was conducted. Total RNA was extracted from AD5-10 hybridomas by TRIzol method (Invitrogen, USA). As template and primers complementing to the IgG constant regions or signal peptide regions, the cDNA encoding for AD5-10 were amplified by RT-PCR. The products were inserted into pMD18-T vector (Bao Biologicals Co. Dalian). The cDNA sequences of AD5-10 were determined by automatic DNA sequencer (Boya Co. Shanghai). The amino acid sequences were deduced from the nucleotide sequences of the said cDNA.

The following primers were used during the cDNA cloning, wherein some of them are degenerate primers, such as K=G/T, M=A/C, R=A/G, S=C/Q W=A/T, Y=C/T,

```
PLSU1:    ATG GAG ACA GAC ACA CTC CTG CTA T

PLSU2:    ATG GAT TTT CAA GTG CAG ATT TTC AG

PLSU3:    ATG GAG WCA CAK WCT CAG GTC TTT RTA

PLSU4:    ATG KCC CCW RCT CAG YTY CTK GT

PLSU5:    ATG AAC TTG CCT GTT AGG CTG TTG
```

```
PLSU6:    ATG ATG AGT CCT GCC CAG TTC CTG

PHSU1:    ATG GRA TGS AGC TGK GTM ATS CTC TT

PHSU2:    ATG RAC TTC GGG YTC AGC TKG RTT TT

PHSU3:    ATG GCT GTC TTG GGG CTG CTC TTC T

PHSU4:    ATG GRA TGG AGC TGG GTG TTT MTS TT

PHSU5:    TGA GCG TSA CCG CCG GCG TGC T

PHSU10:   TTG CTA TTC CTG ATG GCA GCT GC

PLCD:     TTA ACA CTC ATT CCT GTT GA

PHCD:     TTT ACC AGG AGA GCG GGA GAG

PHCD3:    TTT ACC AGG GGA GCG AGA CAG GTT
```

What is claimed is:

1. A monoclonal antibody which binds specifically to TRAIL receptor DR-5, said monoclonal antibody comprising a light chain which has a variable region, with three CDR regions, wherein CDR1 consists of amino acids 24-39 of SEQ ID NO: 1, CDR2 consists of amino acids 55-61 of SEQ ID NO: 1, and CDR3 consists of amino acids 94-102 of SEQ ID NO: 1, and a heavy chain which has a variable region with three CDR regions wherein the first heavy chain CDR region consists of amino acids 31-35 of SEQ ID NO: 2, the second heavy chain CDR region consists of amino acids 50-66 of SEQ ID NO: 2, and the third heavy chain CDR region consists of amino acids 99-101 of SEQ ID NO: 2.

2. The monoclonal antibody of claim 1, comprising SEQ ID NO: 1 and SEQ ID NO: 2.

3. A hybridoma cell line which produces the monoclonal antibody of claim 2.

4. The hybridoma cell line of claim 3, designated by deposition number CGMCC No. 1192.

5. A method for treating a subject suffering from a cancer expressing DR-5, comprising administering to said subject an amount of (i) a murine monoclonal antibody which specifically binds to the extracellular domain of DR-5, (ii) a Fab fragment of (i), or (iii) a F(ab')2 fragment of (i), in an amount sufficient to alleviate said cancer, wherein said monoclonal antibody is the antibody of claim 1.

* * * * *

SEQUENCE LISTING

<160> NUMBER OF SEQ ID NOS: 19

<210> SEQ ID NO 1
<211> LENGTH: 113
<212> TYPE: PRT
<213> ORGANISM: mus musculus

<400> SEQUENCE: 1

Asp Val Val Met Thr Gln Thr Pro Leu Ser Leu Pro Val Ser Leu
                  5                  10                  15

Gly Asp Gln Ala Ser Ile Ser Cys Arg Ser Ser Gln Ser Leu Val
                 20                  25                  30

His Ser Asn Gly Asn Thr Tyr Leu His Trp Tyr Leu Gln Lys Pro
                 35                  40                  45

Gly Gln Ser Pro Lys Leu Leu Ile Tyr Lys Val Ser Asn Arg Phe
                 50                  55                  60

Ser Gly Val Pro Asp Arg Phe Ser Gly Ser Gly Ser Gly Thr Asp
                 65                  70                  75

Phe Thr Leu Lys Ile Ser Arg Val Glu Ala Glu Asp Leu Gly Val
                 80                  85                  90

Tyr Phe Cys Phe Gln Ser Thr His Val Pro His Thr Phe Gly Gly
                 95                 100                 105

Gly Thr Lys Leu Glu Ile Lys Arg
                110

<210> SEQ ID NO 2
<211> LENGTH: 112
<212> TYPE: PRT
<213> ORGANISM: mus musculus

<400> SEQUENCE: 2

Gln Ile Gln Leu Val Gln Ser Gly Pro Glu Leu Lys Lys Pro Gly
                  5                  10                  15

Glu Thr Val Lys Ile Ser Cys Lys Ala Ser Gly Tyr Thr Phe Thr
                 20                  25                  30

Asp Phe Ser Met Asn Trp Val Lys Gln Ala Pro Gly Lys Gly Leu
                 35                  40                  45

Lys Trp Met Gly Trp Ile Asn Thr Glu Thr Gly Glu Pro Thr Tyr

|  | 50 | 55 | 60 |  |
|---|---|---|---|---|

Ala Asp Asp Phe Lys Gly Arg Phe Ala Leu Ser Met Glu Thr Ser
             65                      70                      75

Ala Ser Thr Ala Tyr Leu Gln Ile Asn Asn Leu Lys Asn Glu Asp
             80                      85                      90

Thr Ala Thr Tyr Phe Cys Val Arg Ile Asp Tyr Trp Gly Gln Gly
             95                     100                  105

Thr Thr Leu Thr Val Ser Ser
            110

```
<210> SEQ ID NO 3
<211> LENGTH: 29
<212> TYPE: DNA
<213> ORGANISM: Artificial sequence
<220> FEATURE:
<223> OTHER INFORMATION: DNA primer

<400> SEQUENCE: 3
ggcatgccat ggagtctgct ctgatcacc                                    29

<210> SEQ ID NO 4
<211> LENGTH: 31
<212> TYPE: DNA
<213> ORGANISM: Artificial sequence
<220> FEATURE:
<223> OTHER INFORMATION: DNA primer

<400> SEQUENCE: 4
gcgcggatcc ttagatgcct gagagagaac a                                 31

<210> SEQ ID NO 5
<211> LENGTH: 25
<212> TYPE: DNA
<213> ORGANISM: Artificial sequence
<220> FEATURE:
<223> OTHER INFORMATION: DNA primer

<400> SEQUENCE: 5
atggagacag acacactcct gctat                                        25

<210> SEQ ID NO 6
<211> LENGTH: 26
<212> TYPE: DNA
<213> ORGANISM: Artificial sequence
<220> FEATURE:
<223> OTHER INFORMATION: DNA primer

<400> SEQUENCE: 6
atggattttc aagtgcagat tttcag                                       26

<210> SEQ ID NO 7
<211> LENGTH: 27
<212> TYPE: DNA
<213> ORGANISM: Artificial sequence
<220> FEATURE:
<223> OTHER INFORMATION: DNA primer

<400> SEQUENCE: 7
atggagwcac akwctcaggt ctttrta                                      27

<210> SEQ ID NO 8
<211> LENGTH: 23
<212> TYPE: DNA
<213> ORGANISM: Artificial sequence
```

```
<220> FEATURE:
<223> OTHER INFORMATION: DNA primer

<400> SEQUENCE: 8
atgkccccwr ctcagytyct kgt                                          23

<210> SEQ ID NO 9
<211> LENGTH: 24
<212> TYPE: DNA
<213> ORGANISM: Artificial sequence
<220> FEATURE:
<223> OTHER INFORMATION: DNA primer

<400> SEQUENCE: 9
atgaacttgc ctgttaggct gttg                                         24

<210> SEQ ID NO 10
<211> LENGTH: 24
<212> TYPE: DNA
<213> ORGANISM: Artificial sequence
<220> FEATURE:
<223> OTHER INFORMATION: DNA primer

<400> SEQUENCE: 10
atgatgagtc ctgcccagtt cctg                                         24

<210> SEQ ID NO 11
<211> LENGTH: 26
<212> TYPE: DNA
<213> ORGANISM: Artificial sequence
<220> FEATURE:
<223> OTHER INFORMATION: DNA primer

<400> SEQUENCE: 11
atggratgsa gctgkgtmat sctctt                                       26

<210> SEQ ID NO 12
<211> LENGTH: 26
<212> TYPE: DNA
<213> ORGANISM: Artificial sequnce
<220> FEATURE:
<223> OTHER INFORMATION: DNA primer

<400> SEQUENCE: 12
atgracttcg ggytcagctk grtttt                                       26

<210> SEQ ID NO 13
<211> LENGTH: 25
<212> TYPE: DNA
<213> ORGANISM: Artificial sequence
<220> FEATURE:
<223> OTHER INFORMATION: DNA primer

<400> SEQUENCE: 13
atggctgtct tggggctgct cttct                                        25

<210> SEQ ID NO 14
<211> LENGTH: 26
<212> TYPE: DNA
<213> ORGANISM: Artificial sequence
<220> FEATURE:
<223> OTHER INFORMATION: DNA primer

<400> SEQUENCE: 14
atggratgga gctgggtgtt tmtstt                                       26
```

```
<210> SEQ ID NO 15
<211> LENGTH: 22
<212> TYPE: DNA
<213> ORGANISM: Artificial sequence
<220> FEATURE:
<223> OTHER INFORMATION: DNA primer

<400> SEQUENCE: 15
tgagcgtsac cgccggcgtg ct                                              22

<210> SEQ ID NO 16
<211> LENGTH: 23
<212> TYPE: DNA
<213> ORGANISM: Artificial sequence
<220> FEATURE:
<223> OTHER INFORMATION: DNA primer

<400> SEQUENCE: 16
ttgctattcc tgatggcagc tgc                                             23

<210> SEQ ID NO 17
<211> LENGTH: 20
<212> TYPE: DNA
<213> ORGANISM: Artificial sequence
<220> FEATURE:
<223> OTHER INFORMATION: DNA primer

<400> SEQUENCE: 17
ttaacactca ttcctgttga                                                 20

<210> SEQ ID NO 18
<211> LENGTH: 21
<212> TYPE: DNA
<213> ORGANISM: Artificial sequence
<220> FEATURE:
<223> OTHER INFORMATION: DNA primer

<400> SEQUENCE: 18
tttaccagga gagcgggaga g                                               21

<210> SEQ ID NO 19
<211> LENGTH: 24
<212> TYPE: DNA
<213> ORGANISM: Artificial sequence
<220> FEATURE:
<223> OTHER INFORMATION: DNA primer

<400> SEQUENCE: 19
tttaccaggg gagcgagaca ggtt                                            24
```